United States Patent
Gallant

(12) 
(10) Patent No.: US 6,637,049 B2
(45) Date of Patent: Oct. 28, 2003

(54) PERSONAL CARE MODULE

(75) Inventor: Dennis J. Gallant, Harrison, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 10/061,597

(22) Filed: Feb. 1, 2002

(65) Prior Publication Data

US 2002/0174483 A1 Nov. 28, 2002

Related U.S. Application Data

(60) Provisional application No. 60/293,949, filed on May 25, 2001.

(51) Int. Cl.⁷ .................................................. A47K 4/00
(52) U.S. Cl. ................................ 4/664; 4/300.2; 4/643; 312/249.7
(58) Field of Search .......................... 4/300.2, 625, 626, 4/664, 665, 476, 549, 643; 312/249.7, 249.8, 300, 309, 322

(56) References Cited

U.S. PATENT DOCUMENTS

| | | | | |
|---|---|---|---|---|
| 41,602 A | * | 2/1864 | Campbell .................. 4/664 X |
| 376,871 A | * | 1/1888 | Elwell ............................ 4/665 |
| 877,196 A | * | 1/1908 | Hubert ..................... 4/665 X |
| 2,495,201 A | * | 1/1950 | Snowball ...................... 4/664 |
| 2,894,794 A | | 7/1959 | Mays ........................ 312/313 |
| 3,241,850 A | | 3/1966 | Propst .................. 280/33.998 |
| 3,250,583 A | | 5/1966 | Phillips ....................... 433/27 |
| 3,267,955 A | | 8/1966 | Logan et al. ................ 137/357 |
| 3,462,920 A | | 8/1969 | Denny .......................... 55/413 |
| 3,514,794 A | | 6/1970 | Pofferi ............................ 5/2.1 |
| 3,829,906 A | | 8/1974 | McPhee ........................ 4/312 |
| 3,846,853 A | | 11/1974 | Jacobsson ..................... 5/87.1 |
| 3,921,345 A | | 11/1975 | Damico .......................... 52/28 |
| 4,072,157 A | | 2/1978 | Wines, Jr. et al. .......... 4/625 X |
| 4,104,710 A | | 8/1978 | Damico et al. ............. 362/130 |
| 4,129,122 A | | 12/1978 | Dout et al. .................... 600/21 |
| 4,475,322 A | | 10/1984 | Russo et al. ................... 52/27 |
| 4,612,679 A | | 9/1986 | Mitchell |
| 4,646,211 A | | 2/1987 | Gallant et al. .............. 362/149 |
| 4,753,055 A | | 6/1988 | Durham, Jr. ................... 52/28 |
| 4,821,470 A | | 4/1989 | Kappers et al. ............ 52/220.1 |
| 5,097,550 A | | 3/1992 | Marra, Jr. |

(List continued on next page.)

FOREIGN PATENT DOCUMENTS

| | | |
|---|---|---|
| DE | 200 18 317 U1 | 2/2001 |
| EP | 0 311 336 | 4/1989 |
| EP | 0 481 942 A1 | 4/1992 |
| EP | 0947187 | 10/1999 |
| EP | 0 966 944 A2 | 12/1999 |
| EP | 969241 * | 1/2000 |
| EP | 1030143 | 8/2000 |
| GB | 1 490 381 | 11/1977 |
| WO | WO 94/20784 | 9/1994 |
| WO | WO 98/33419 | 8/1998 |
| WO | WO 98/50840 | 11/1998 |
| WO | WO 01/33529 | 5/2001 |

OTHER PUBLICATIONS

Product Brochure from Hill–Rom Services, Inc. (published 2001).
Hill–Rom Future of Care 2.0 Videotape, date unknown, Copyright Hill–Rom Company, Inc.
Hill–Rom Future of Care Version 4.0 Videotape, 1999, Copyright Hill–Rom Company, Inc.

*Primary Examiner*—Robert M. Fetsuga
(74) *Attorney, Agent, or Firm*—Barnes & Thornburg

(57) ABSTRACT

A personal care module for use by a patient within a room of a healthcare facility comprises a first washing station, at least one of a toilet and a second washing station, and a housing coupled to the first washing station and the at least one of the toilet and the second washing station.

22 Claims, 4 Drawing Sheets

U.S. PATENT DOCUMENTS

| | | |
|---|---|---|
| 5,107,636 A | 4/1992 | Schindele et al. ............. 52/27 |
| 5,108,063 A | 4/1992 | Koerber, Sr. et al. .... 248/284.1 |
| D331,621 S | 12/1992 | Tapolcai |
| 5,174,285 A | 12/1992 | Fontenot ..................... 128/400 |
| 5,247,962 A | 9/1993 | Walker ........................ 137/360 |
| 5,304,213 A | 4/1994 | Berke et al. ................ 607/104 |
| 5,314,243 A | 5/1994 | McDonald et al. ......... 312/215 |
| 5,319,816 A | 6/1994 | Ruehl |
| 5,465,438 A * | 11/1995 | Allman et al. ................ 4/626 |
| 5,507,734 A | 4/1996 | Everett, Jr. et al. |
| 5,555,582 A | 9/1996 | Jerideau ........................ 5/600 |
| 5,577,279 A | 11/1996 | Foster et al. .................... 5/618 |
| 5,623,948 A | 4/1997 | VanMorris .................. 128/845 |
| 5,653,064 A | 8/1997 | Kappers et al. .............. 52/36.4 |
| 5,702,115 A | 12/1997 | Pool |
| 5,708,997 A | 1/1998 | Foster et al. .................... 5/618 |
| 5,878,536 A | 3/1999 | Demmitt et al. ............. 52/36.4 |
| 5,933,888 A | 8/1999 | Foster et al. .................... 5/604 |
| 6,006,379 A | 12/1999 | Hensley ........................ 5/618 |
| 6,112,345 A | 9/2000 | Foster et al. ................... 5/81 R |
| 6,213,481 B1 | 4/2001 | Marchese et al. ............. 280/35 |

* cited by examiner

PERSONAL CARE MODULE

CROSS-REFERENCE TO RELATED APPLICATION

This application claims priority under 35 U.S.C. §119(e) to U.S. Provisional Application No. 60/293,949, filed May 25, 2001, which is expressly incorporated by reference herein.

TECHNICAL FIELD

The present disclosure relates to a personal care module. The personal care module is disclosed in the context of being useful for a patient within a room of a healthcare facility. The personal care module is believed to be useful in other applications as well.

BACKGROUND AND SUMMARY

Patients in healthcare facilities, such as hospitals and nursing homes, sometimes have limited mobility. Ambulating to obtain basic personal care services, such as, for example, access to a sink and faucet, a toilet, and a bed pan washer, may be difficult for these individuals without the assistance of a caregiver who may not be available immediately. Such personal services are sometimes located in a restroom attached to the patient's room. This may require the patient to maneuver around one or more beds, furniture, and hospital equipment to reach the restroom. Some patients having limited mobility may prefer easier access to personal care services.

According to this disclosure, a personal care module for use by a patient within a room of a healthcare facility comprises a toilet, a washing station, and a housing coupled to the toilet and the washing station. The washing station has either a sink and a faucet or a bed pan washer. Illustratively, the housing is movable between a first position extending alongside a wall of the room and a second position extending alongside a bed in the room.

Further illustratively, the housing has a first portion and a second portion. The washing station is coupled to the first portion. The toilet is coupled to the second portion. The first portion and the second portion are relatively movable between a third position to cover the toilet and a fourth position to uncover the toilet.

According to another aspect of this disclosure, a personal care module for use by a patient within a room of a healthcare facility comprises a toilet, a washing station having a sink and a faucet, a bed pan washer, and a housing coupled to the toilet, the washing station, and the bed pan washer.

According to another aspect of this disclosure, a personal care module for use by a patient within a room of a healthcare facility comprises a first washing station, a second washing station, and a housing coupled to the first washing station and the second washing station. Illustratively, the first washing station has a sink and a faucet, and the second washing station has a bed pan washer.

Additional features will become apparent to those skilled in the art upon consideration of the following detailed description of illustrative embodiments exemplifying the best mode as presently perceived.

BRIEF DESCRIPTION OF THE DRAWINGS

The detailed description particularly refers to the accompanying figures in which.

DETAILED DESCRIPTION OF THE DRAWINGS

Figure 1:
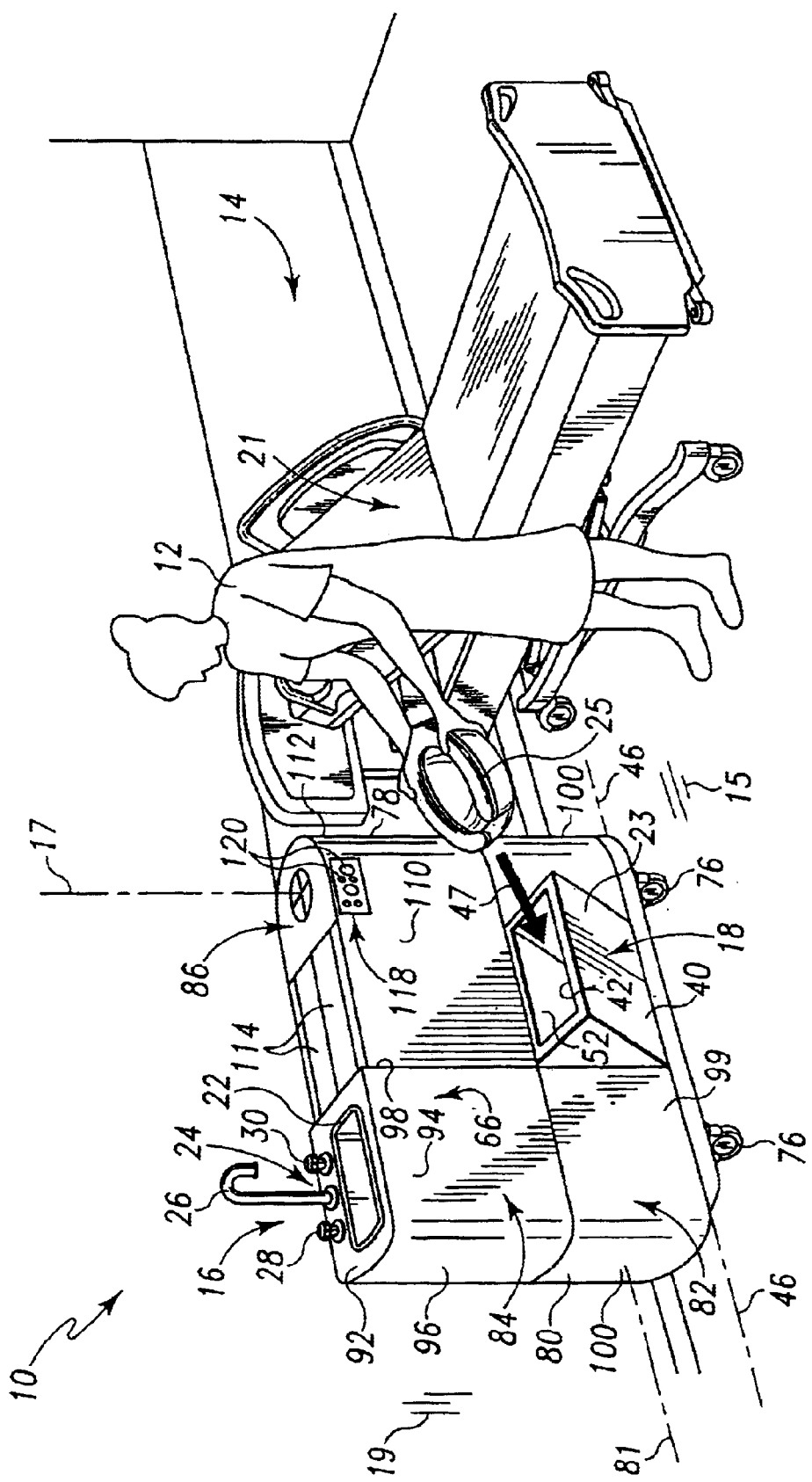
FIG. 1 is a perspective view of a personal care module positioned in a first position extending alongside a wall of a patient's room, the personal care module comprising a first washing station having a sink and a faucet and a second washing station having a bed pan washer.

A personal care module 10 configured for use by a patient 12 in a healthcare facility such as, for example, a hospital or a nursing home is illustrated in FIGS. 1–4. Module 10 is configured to be conveniently located in a room 14 of the healthcare facility for ready access by patient 12 who may have limited mobility. Module 10 is movable along a room floor 15 about a vertical pivot axis 17 in opposite directions indicated by double-head dashed arrow 27 in FIG. 2 between a first position (FIG. 1, FIG. 2 in phantom) extending alongside a room wall 19 and a second position (FIG. 2 in solid, FIG. 3) extending alongside a bed 21 in room 14.

Figure 2:
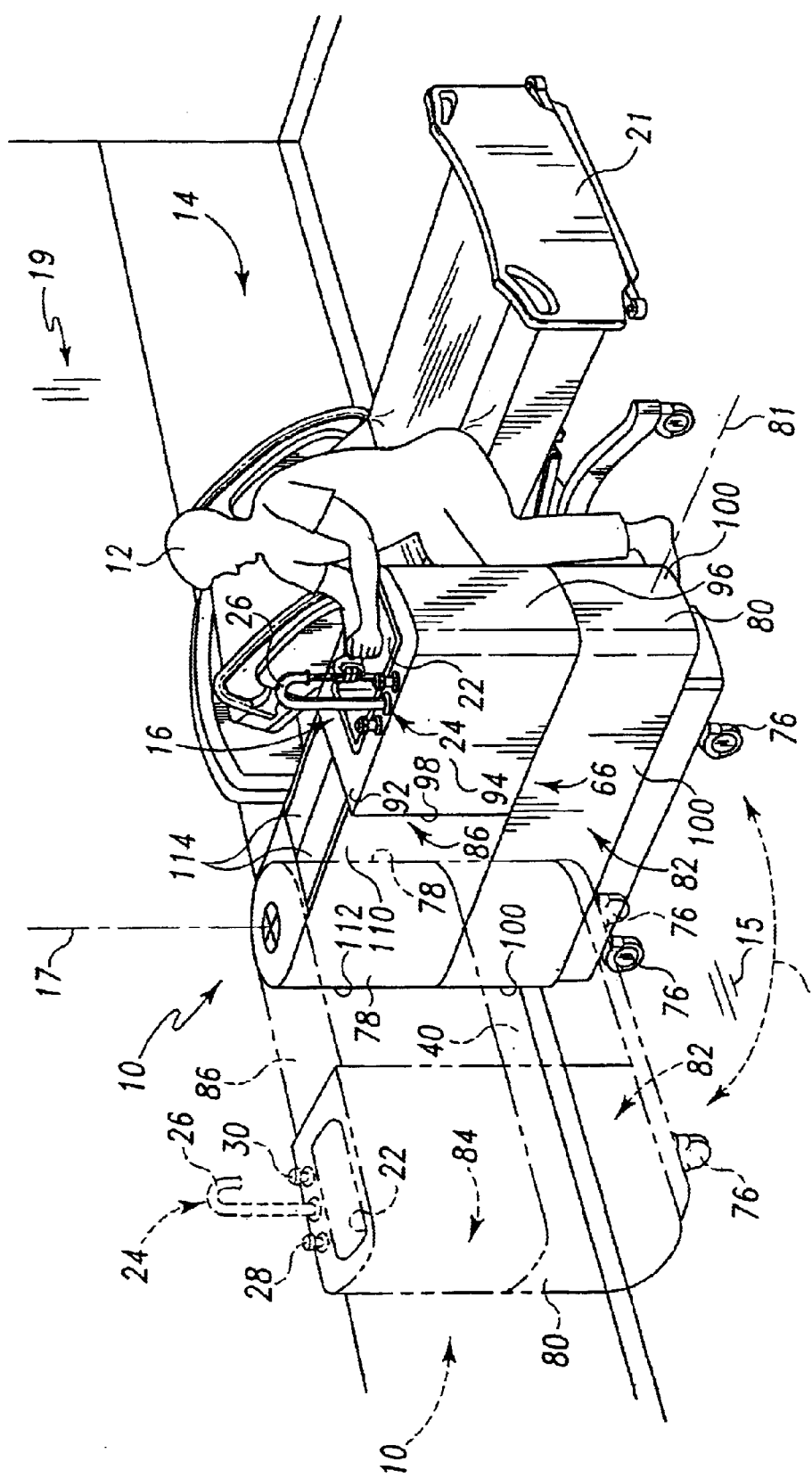
FIG. 2 is a perspective view of the personal care module which is movable along the floor of the room about a pivot axis between the first position (shown in dashed lines) and a second position (shown in solid lines) extending alongside a bed in the room for ready access by the patient.
Figure 3:
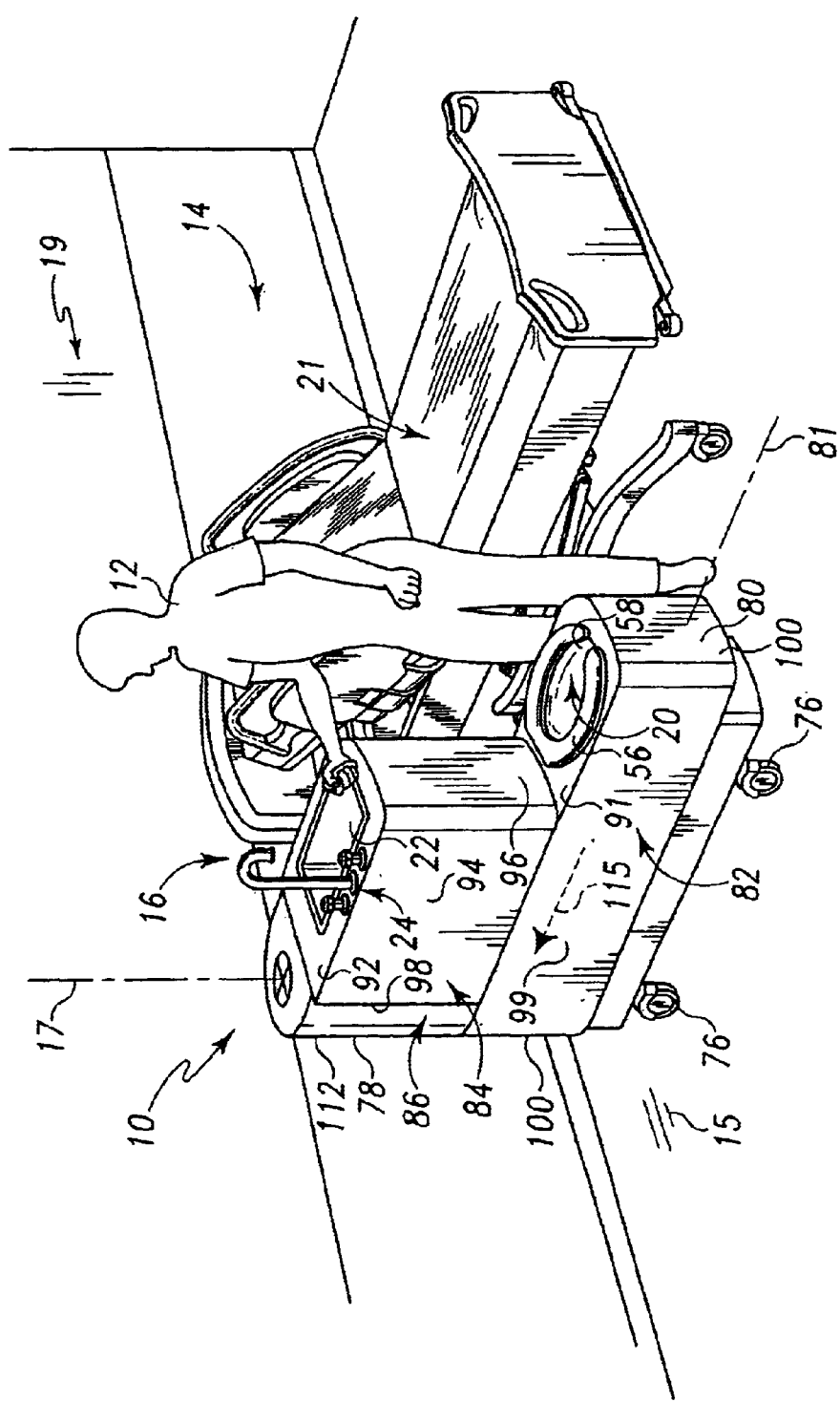
FIG. 3 is a perspective view of the personal care module having a toilet uncovered by an upper portion of a housing of the personal care module upon movement of the upper portion in the direction of the dashed arrow.
Figure 4:
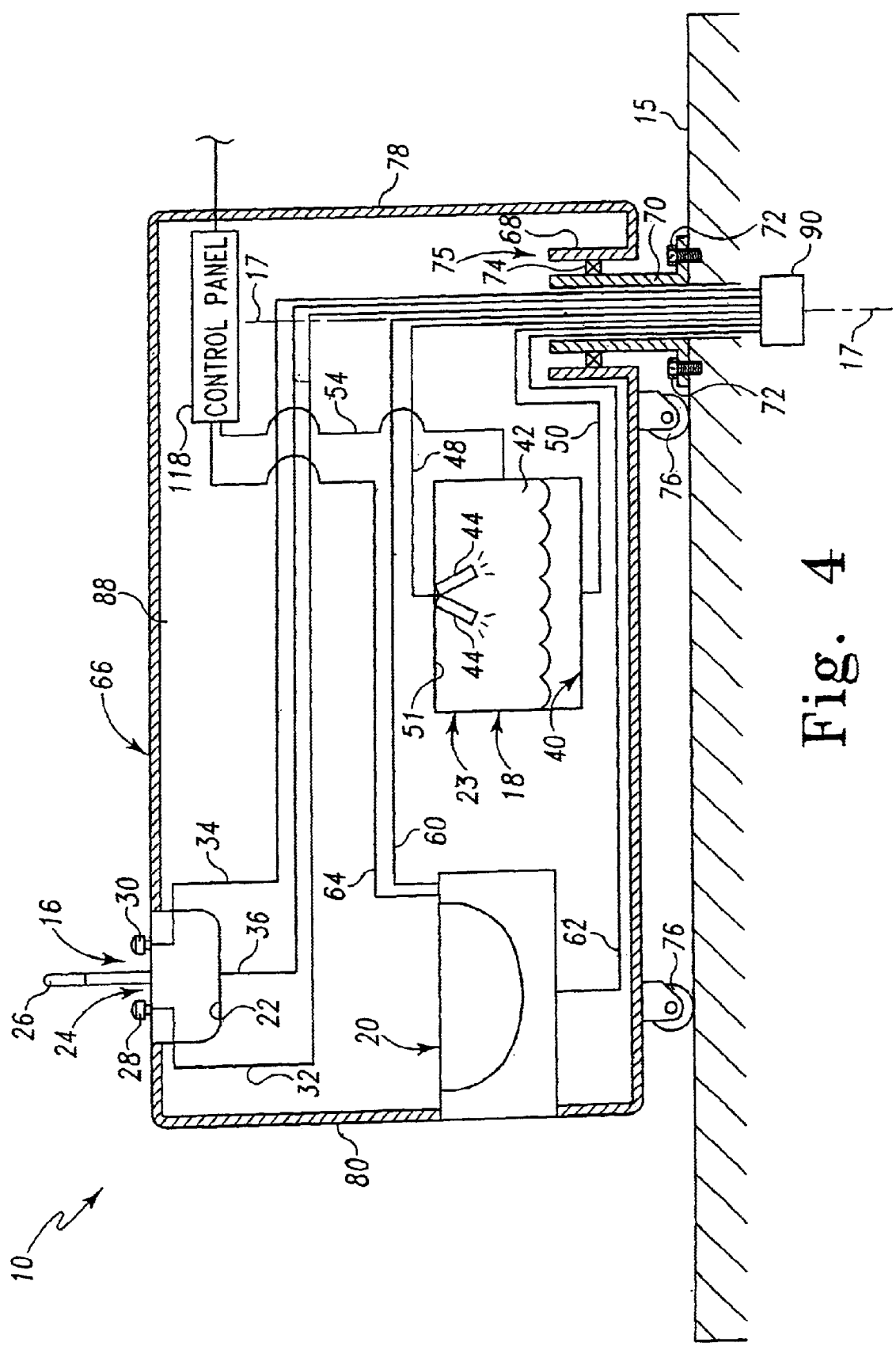
FIG. 4 is a diagrammatic view of the personal care module showing a pivot coupling between the housing and the floor, a control panel coupled to the bed pan washer and the toilet, and supply and drain lines coupled to the first washing station, the bed pan washer, and the toilet and routed through the interior of the housing to the floor of the room.

Personal care module 10 provides a variety of services for patient 12. Module 10 has a first washing station 16 (FIGS. 1–4), a second washing station 18 (FIGS. 1 and 4), and a toilet 20 (FIGS. 3 and 4). Station 16 has a faucet 24 for dispensing water and a sink 22 for draining the water. Station 18 has an automatic bed pan washer 23 for washing a bed pan 25. It is within the scope of this disclosure for module 10 to provide one or more other services in addition to or in place of stations 16, 18 and toilet 20. Such other services include a water purification system, dialysis connections, and urine sampling equipment.

Faucet 24 has a spout 26, a hot water control 28, and a cold water control 30. Other types of faucets are within the scope of this disclosure. For example, in alternative embodiments, the faucet has a single temperature control for hot and cold water. In other alternative embodiments, the spout has a removable nozzle coupled to a flexible tube to dispense water from a variety of positions. A hot water supply line 32 provides hot water to hot water control 28 while a cold water supply line 34 provides cold water to cold water control 30 as shown diagrammatically in FIG. 4. A drain line 36 is coupled to an aperture of a bottom portion of sink 22 to drain water therefrom.

Washer 23 of station 18 has a receptacle 40 for receiving bed pan 25 in an interior region 42 thereof, as illustrated in FIGS. 1 and 4. Washer 23 also has one or more dispensers 44, shown diagrammatically in FIG. 4, for dispensing a cleaning agent such as water and/or a disinfectant into interior region 42 to wash a bed pan 25 positioned therein. Receptacle 40 is movable about a pivot axis 46 between an opened position (FIG. 1) and a closed position (FIG. 2). Bed pan 25 can be inserted in direction of arrow 47 through an opening of receptacle 40 into interior region 42 when receptacle 40 is positioned in its opened position. Bed pan washer 23 washes bed pan 25 after receptacle 40 is pivoted to its closed position. A supply line 48 is coupled to dispensers 44 to provide the cleaning agent thereto. A drain line 50 is coupled to a bottom aperture of receptacle 40 to drain receptacle 40.

Dispensers 44 extend downwardly from an upper wall 51 of bed pan washer 23 into interior region 42 of receptacle 40, as shown diagrammatically in FIG. 4. It is within the scope of this disclosure for a rear wall 52 of receptacle 40, shown in FIG. 1, to have an opening sized to permit passage of dispensers 44 therethrough to accommodate movement of receptacle 40 between its opened and closed positions. In some embodiments, dispensers 44 are movable from an extended position wherein dispensers 44 extend downwardly from upper wall 51 into interior region 42 to wash bed pan 25 and a retracted position wherein dispensers 44 are retracted into corresponding openings in upper wall 53 to accommodate movement of receptacle 40 between its opened and closed positions. In other embodiments, dispensers 44 remain in such a retracted position even during operation of bed pan washer 23. It is within the scope of this disclosure for dispensers 44 to be fixed or movable, such as being rotatable, relative to receptacle 40 during operation of bed pan washer 23.

Toilet 20 has a seat 56 for patient 12 and a receptacle 58, as illustrated in FIG. 3. A water supply line 60 is coupled to toilet 20 to provide water thereto. A drain line 62 is coupled to toilet 20 to drain waste therefrom.

Personal care module 10 has a housing 66, as illustrated in FIGS. 1–4. Housing 66 has a proximal end portion 78 and a distal end portion 80. A longitudinal axis 81 of module 10 extends horizontally through proximal end portion 78 and distal end portion 80. Housing 66 also has a lower housing portion 82, a first upper housing portion 84, and a second upper housing portion 86. Lower housing portion 82 supports upper housing portions 84, 86 for movement therewith as module 10 is pivoted between its first, wall position and its second, bed position. First upper housing portion 84 is movable relative to lower housing portion 82 and second upper housing portion 86 between a toilet-covering, extended position (FIGS. 1, 2, and 4) to cover toilet 20 and a toilet-uncovering, retracted position (FIG. 3) to uncover toilet 20, as discussed in more detail below.

Proximal end portion 78 of lower housing portion 82 has an outer sleeve 68, as illustrated in FIG. 4. An inner sleeve 70 is coupled to floor 15 via fasteners 72 and is positioned inside of first sleeve 68. A bearing 74 engages sleeves 68 and 70 so that module 10 can move about vertical pivot axis 17 between the first, wall position and second, bed position. Thus, sleeves 68 and 70 and bearing 74 cooperate to define a pivot coupling 75 between module 10 and floor 15. Floor-engaging elements 76, such as wheels or casters, are coupled to lower housing portion 82 to facilitate movement of module 10 along floor 15, as illustrated in FIGS. 1–4. In alternative embodiments, lower housing portion 82 has a skirt that hangs downwardly to shield casters 76 from view.

Lines 32, 34, 36, 48, 50, 60, and 62 are routed through an interior region 88 of housing 66 and through inner sleeve 70. Lines 32, 34, 36, 48, 50, 60, and 62 are then coupled to corresponding plumbing lines represented by box 90 and routed through floor 15. Alternatively, lines 32, 34, 36, 48, 50, 60, and 62 are coupled to a headwall mounted to wall 19. At least some portions of lines 32, 34, 36, 48, 50, 60, and 62 are flexible to accommodate the pivoting movement of module 10 between its first, wall position and second, bed position and to accommodate the movement of first upper housing portion 84 between its extended and retracted positions. In some embodiments, drain line 36 includes a rigid portion providing an S-shaped trap that traps solid objects dropped inadvertently into sink 22.

Lower housing portion 82 contains second washing station 18 (FIG. 1) and toilet 20 (FIG. 3). Second washing station 18 is positioned adjacent to proximal end portion 78. Toilet 20 is positioned adjacent to distal end portion 80. Toilet seat 56 is coupled to an upper wall 91 of portion 82. Portion 82 also has side walls 99 and end walls 100 coupled to side walls 99. Side walls 99 and end walls 100 are coupled to upper wall 91. Receptacle 40 of bed pan washer 23 pivots outwardly relative to one of side walls 99 to its opened position (FIG. 1) and pivots inwardly relative thereto to its closed position.

First upper housing portion 84 carries first washing station 16, as illustrated in FIGS. 1–3. Sink 22, spout 26, and hot and cold water controls 28, 30 are mounted to an upper wall 92 of first upper housing portion 84. Portion 84 further has a pair of opposing side walls 94 and an end wall 96 coupled to side walls 94. Side walls 94 and end wall 96 are coupled to upper wall 92. Upper wall 92 and side walls 94 cooperate to define an edge 98 that defines an opening into an interior region of portion 84. The majority of sink 22 is positioned in the interior region of portion 84 between side walls 94.

Second upper housing portion 86 has side walls 110, an end wall 112 coupled to side walls 110, and a pair of doors 114, as illustrated in FIGS. 1–3. Control panel 118 is mounted to one of side walls 110. Each door 114 is coupled to a top portion of one of side walls 110 for movement, such as by pivoting, between a raised position (FIGS. 1 and 2) wherein doors 114 are positioned to lie in generally horizontal, co-planar relation with one another and a lowered position wherein each door 114 extends downwardly alongside the respective side wall 110.

First upper housing portion 84 is movable on lower housing portion 82 along longitudinal axis 81 between its toilet-covering, extended position FIGS. 1, 2, and 4) and its toilet-uncovering, retracted position (FIG. 3). Housing portions 84 and 86 are arranged in telescoping relation with one another. Housing portion 84 is slightly larger than housing portion 86 so that a majority of housing portion 86 is positioned to lie in the interior region of housing portion 84 when housing portion 84 is positioned in its retracted position. Thus, housing portion 84 covers housing portion 86 when housing portion 84 is positioned in its retracted position.

During movement of housing portion 84 from its extended position to its retracted position in a direction indicated by arrow 115 (FIG. 3), doors 114 move automatically from their raised position to their lowered position to allow sink 22 to move into a space between doors 114. When housing portion 84 returns to its extended position, doors 114 move automatically from their lowered position to their raised position. It is within the scope of this disclosure for suitable devices, such as cables, linkages, or cam mechanisms, to be used to couple the movement of housing portion 84 to doors 114.

In some embodiments, side walls 94 of first upper housing portion 84 are configured to mate with corresponding tracks (not shown) mounted on upper wall 91 or upper portions of side walls 99 to allow movement of first upper housing portion 84 between its extended and retracted positions. In other embodiments, rollers (not shown) are coupled to a bottom portion of each side wall 94 to ride on the tracks.

First washing station 16 and toilet 20 are aligned vertically with one another such that first washing station 16 is positioned above toilet 20 when first upper housing portion 84 is positioned in its extended position. First washing station 16 and toilet 20 are offset vertically from one another when first upper housing portion 84 is positioned in its retracted position. First washing station 16 and second washing station 18 are aligned vertically with one another such that first washing station 16 is positioned above second washing station 18 when first upper housing portion 84 is positioned in its retracted position.

A control panel 118 for controlling module 10 is coupled to one of side walls 110 of second upper housing portion 86, as illustrated in FIG. 1. Control panel 118 has user inputs 120 that are engaged to control various functions of module 10. Control panel 118 is coupled to bed pan washer 23 via an electrical conductor 54 to control its washing cycles. It is within the scope of this disclosure for module 10 to have sensors (not shown) coupled to control panel 118 to sense the presence of bed pan 25 in receptacle 40 and to sense the position of receptacle 40 so that bed pan 25 is washed automatically upon movement of receptacle 40 to its closed position. Control panel 118 further controls flushing of toilet 20 via electrical conductor 64 in response to, for example, one of user inputs 120 or a proximity sensor (not shown) mounted to sense when toilet 20 is no longer being used. Alternatively, toilet 20 is flushed manually via a mechanical lever. It is also within the scope of this disclosure for one or more of user inputs 120 to control powered movement of module 10 between its first, wall position and its second, bed position and one or more of user inputs 120 to control movement of first upper housing portion 84 between its extended and retracted positions.

Personal care module 10 is operable in both its first, wall position and its second, bed position or in positions therebetween. When module 10 is in its first, wall position, patient 12 can use first and second washing stations 16, 18 (FIG. 1) and can use toilet 20 upon retraction of first upper housing portion 84. When module 10 is in its second, bed position, patient 12 sitting on bed 21 is able to use first washing station 16 for hand washing or to obtain water for drinking without having to exit bed 21, as illustrated in FIG. 2. In addition, when module 10 is in its second, bed position, patient 12 sitting on bed 21 is able to move first upper housing portion 84 toward wall 19 of room in a direction indicated by a dashed arrow 115 from its extended position to its retracted position to expose toilet 20. Patient 12 is then able to move a short distance from a seated position on bed 21 to a seated position on toilet seat 56. During movement from bed 21 to toilet seat 56, a patient having limited mobility may steady himself or herself by holding to portions of module 10 as illustrated in FIG. 3.

Although certain illustrative embodiments have been disclosed in detail, variations and modifications exist within the scope and spirit of the invention as described and defined in the following claims.

What is claimed is:

1. A personal care module for use by a patient within a room of a healthcare facility, the personal care module comprising
    a toilet,
    a washing station having a sink and a faucet,
    a bed pan washer, and
    a housing coupled to the toilet, the washing station, and the bed pan washer, the housing comprising a movable portion, the washing station being coupled to the movable portion for movement therewith relative to the toilet and the bed pan washer.

2. The personal care module of claim 1, wherein the housing is adapted to be coupled to a floor of the room for movement of the housing about a pivot axis.

3. The personal care module of claim 2, wherein the housing has a proximal end portion and a distal end portion, the proximal end portion is adapted to be coupled to the floor to establish the pivot axis, the bed pan washer is positioned adjacent to the proximal end portion, and the toilet is positioned adjacent to the distal end portion.

4. The personal care module of claim 1, further comprising a floor-engaging element adapted to engage a floor of the room to facilitate movement of the housing along the floor.

5. The personal care module of claim 1, wherein the washing station is movable with the movable portion between a first position over the toilet and a second position over the bed pan washer.

6. The personal care module of claim 5, wherein the housing comprises a lower portion on which the movable portion is movable, and the toilet and the bed pan washer are coupled to the lower portion.

7. The personal care module of claim 1, wherein the bed pan washer comprises a receptacle to receive and support a bed pan, and the receptacle is movable relative to the housing between an opened position to receive the bed pan and a closed position to allow washing of the bed pan.

8. The personal care module of claim 7, wherein the receptacle is movable about a pivot axis between the opened and closed positions.

9. The personal care module of claim 1, comprising a pivot coupling for movement of the personal care module about a pivot axis.

10. A personal care module for use by a patient within a room of a healthcare facility, the personal care module comprising
    a toilet,
    a washing station having a sink and a faucet,
    a bed pan washer, and
    a housing coupled to the toilet, the washing station, and the bed pan washer, wherein the housing is adapted to be coupled to a floor of the room for movement of the housing about a pivot axis, the housing has a proximal end portion and a distal end portion, the proximal end portion is adapted to be coupled to the floor to establish the pivot axis, the bed pan washer is positioned adjacent to the proximal end portion, the toilet is positioned adjacent to the distal end portion, the housing includes a first portion and a second portion, the washing station is coupled to the first portion, the toilet and the bed pan washer are coupled to the second portion, and the washing station and the first portion are movable along a second axis between a first position wherein the first portion covers the toilet and a second position wherein the first portion uncovers the toilet.

11. The personal care module of claim 10, wherein the pivot axis and the second axis are transverse to one another.

12. A personal care module for use by a patient within a room of a healthcare facility the personal care module comprising
    a toilet,
    a washing station having a sink and a faucet,
    a bed pan washer, and
    a housing coupled to the toilet, the washing station, and the bed pan washer, wherein the washing station is movable relative to the toilet and the bed pan washer along a longitudinal axis of the housing.

13. The personal care module of claim 12, wherein the housing has a first portion and a second portion, the washing station is coupled to the first portion, the toilet and the bed pan washer are coupled to the second portion, and the washing station and the first portion are movable along the longitudinal axis between a first position wherein the first portion covers the toilet and a second position wherein the first portion uncovers the toilet.

14. A personal care module for use by a patient within a room of a healthcare facility wherein the room has a floor, the personal care module comprising a toilet, a washing station having a sink and a faucet, a bed pan washer, a housing having a first portion and a second portion, the washing station being coupled to the first portion, the toilet and the bed pan washer being coupled to the second portion, the personal care module being movable along the floor between a first position and a second position, the first portion and the second portion being relatively movable between a third position to cover the toilet and a fourth position to uncover the toilet.

15. The personal care module of claim 14, wherein the second portion is adapted to be coupled to the floor for movement of the personal care module about a pivot axis between the first position and the second position.

16. The personal care module of claim 15, wherein the first portion is movable along a longitudinal axis of the personal care module between the third position and the fourth position.

17. The personal care module of claim 16, wherein the pivot axis and the longitudinal axis are transverse to one another.

18. The personal care module of claim 14, wherein the washing station is positioned above the toilet when the first portion is positioned in the third position.

19. The personal care module of claim 18, wherein the washing station is positioned above the bed pan washer when the first portion is positioned in the fourth position.

20. The personal care module of claim 14, wherein the housing has a third portion that is positioned in telescoping relation with the first portion.

21. The personal care module of claim 20, wherein the first portion covers the third portion when the first portion is positioned in the fourth position.

22. The personal care module of claim 14, wherein the bed pan washer has a receptacle adapted to receive a bed pan and coupled to the second portion for movement between an opened position and a closed position.

* * * * *